United States Patent
Houghton et al.

(10) Patent No.: US 6,328,969 B1
(45) Date of Patent: Dec. 11, 2001

(54) METHOD AND COMPOSITIONS FOR STIMULATION OF AN IMMUNE RESPONSE TO A DIFFERENTIATION ANTIGEN STIMULATED BY AN ALTERED DIFFERENTIATION ANTIGEN

(75) Inventors: Alan N. Houghton, New York, NY (US); Clarissa Naftzger, San Carlos, CA (US); Setaluri Vijayasaradhi, Winston-Salem, NC (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/308,697

(22) PCT Filed: Dec. 10, 1997

(86) PCT No.: PCT/US97/22669

§ 371 Date: May 21, 1999

§ 102(e) Date: May 21, 1999

(87) PCT Pub. No.: WO98/25574

PCT Pub. Date: Jun. 18, 1998

Related U.S. Application Data

(60) Provisional application No. 60/032,535, filed on Dec. 10, 1996, and provisional application No. 60/036,419, filed on Feb. 18, 1997.

(51) Int. Cl.$^7$ .......................... A61K 39/08; A61K 48/00; A01N 63/00; A01N 65/00; C12Q 1/00
(52) U.S. Cl. .................... 424/184.1; 424/93.1; 424/93.2; 424/93.7; 424/277.1; 435/4; 435/7.21; 435/7.23; 435/69.1; 435/252.3; 435/325; 435/348; 435/352; 435/354; 435/366
(58) Field of Search ................................. 424/93.1, 93.2, 424/93.7, 277.1, 184.1; 435/4, 7.21, 7.23, 69.1, 252.3, 325, 348, 352, 354, 366

(56) References Cited

U.S. PATENT DOCUMENTS

| 5,314,813 | 5/1994 | Peterson | 435/172.3 |
| 5,397,703 | 3/1995 | DeBoer | 435/172.2 |

FOREIGN PATENT DOCUMENTS

| WO 92/17205 | 10/1992 | (WO) . |
| WO 98/04720 | 2/1998 | (WO) . |

OTHER PUBLICATIONS

Osband and Ross. Problems in the investigational study and clinical use of cancer immunotherapy. Immunol. Today 11(6): 193–195, 1990.*
Guru, Trisha. Systems for Identifying new drugs are often faulty. Science 278:1041–1042, 1997.*
Naftzger et al. Immune response to response to a differentiation antigen induced by altered antigen: A study of tumor rejection and autoimmunity. Proc. Natl. Acad. Sci. USA 93:14809–14814, 1996.*
Naftzger, Clarissa. Melanosomal glycoproteins as autoantigens: generation of autoantibodies against murine gp75. Dissertation Abstracts Internation 60(02–B):569, 1994.*
C. Cabañas, F. Sanchez–Madrid, A. Acevedo, T. Bellon, J.M. Fernandez, V. Larraga, and C. Bernabeu, "Characterization of a CD11c–Reactive Monoclonal Antibody (HC1/1) Obtained by Immunizing with Phorbol Ester Differentiated U937 Cells" *Hybridoma*, 1988, vol. 7, No. 2, pp. 167–177.
Ausubel, F.M., Brent, R., Kingston, R.E., Moore, D.D., Seidman, J.G., Smith, J.A., Struhl, K., "Expression of Proteins in Insect Cells Using Baculoviral Vectors," *Current Protocols in Molecular Biology*, Greene Publishing and Wiley–Interscience, 1990, vol. 2, 16.8.1–16.11.7.
D.M. Pardoll, and A.M. Beckerleg, "Exposing the Immunology of Naked DNA Vaccines," *Immunity*, Cell Press, 1995, vol. 3, pp. 165–169.
C.J. Tiffs, R.L. Proia, and R.D. Camerini–Otero, "The Folding and Cell Surface Expression of CD4 Requires Glycosylation," *The Journal of Biological Chemistry*, 1992, vol. 267, No. 5, pp. 3266–3273.
J.B. Ulmer, J.J. Donnelly, S.E. Parker, G.H. Rhodes, P. L. Felgner, V.J. Dwarki, S.H. Gromkowski, R.R. Deck, C.M. DeWitt, A. Friedman, L.A. Hawe, K.R. Leander, D. Martinez, H.C. Perry, J.W. Shiver, D.L. Montgomery, M.A. Liu, "Heterologous Protection Against Influenza by Injection of DNA Encoding a Viral Protein," *Science*, 1993, vol. 259, pp. 1745–1749.

(List continued on next page.)

*Primary Examiner*—Sheela Huff
*Assistant Examiner*—Alana M. Harris
(74) *Attorney, Agent, or Firm*—Oppedahl & Larson LLP

(57) ABSTRACT

Tolerance of the immune system for self differentiation antigens can be overcome and an immune response stimulated by administration of a therapeutic differentiation antigen. The therapeutic differentiation antigen is altered with respect to the target differentiation antigen in the individual being treated (i.e., the differentiation antigen to which an immune response is desired) in one of three ways. First, the therapeutic differentiation antigen may be syngeneic with the target differentiation antigen, provided that therapeutic differentiation antigen is expressed in cells of a species different from the individual being treated. For example, a human differentiation antigen expressed in insect or other non-human host cells can be used to stimulate an immune response to the differentiation antigen in a human subject. Second, the therapeutic differentiation antigen may be a mutant form of a syngeneic differentiation antigen, for example a glycosylation mutant. Third, the therapeutic differentiation antigen may be a differentiation antigen (wild-type or mutant) of the same type from a species different from the individual being treated. For example, a mouse differentiation antigen can be used to stimulate an immune response to the corresponding differentiation antigen in a human subject. Administration of altered antigens in accordance with the invention results in an effective immunity against the original antigen expressed by the cancer in the treated individual.

19 Claims, 1 Drawing Sheet

OTHER PUBLICATIONS

N.K. Nanda and E.E. Sercarz, "Induction of Anti–Self–Immunity to Cure Cancer," *Cell*, Cell Press, 1995, vol. 82, pp. 13–17.

B. Bouchard, B. B. Fuller, S. Vijayasaradhi, and A. N. Houghton, "Induction of Pigmentation in Mouse Fibroblasts by Expression of Human Tyrosinase cDNA," *J. Exp. Med.*, 1989, vol. 169, pp. 2029–2042.

S. Vijayasaradhi, Y. Xu, B. Bouchard, and A.N. Houghton, "Intracellular Sorting and Targeting of Melanosomal Membrane Proteins: Identification of Signals for Sorting of the Human Brown Locus Protein, GP75," *The Journal of Cell Biology*, Rockefeller University Press, 1995, vol. 130, No. 4, 807–820.

J.F. Rowell, A.L. Ruff, F.G. Guarnieri, K.Staveley–O'Carroll, X. Lin, J. Tang, J.T., Aug., and R.F. Siliciano, "Lysosome–Associated Membrane Protein–1–Mediated Targeting of the HIV–1 Envelope Protein to an Endosomal/Lysosomal Compartment Enhances Its Presentation to MHC Class II–Restricted T Cells," *The Journal of Immunology*, 1995, pp. 1818–1828.

S. Vijayasaradhi, B. Bouchard, and A.N. Houghton, "The Melanoma Antigen gp75 is the Human Homologue of the Mouse b (Brown) Locus Gene Product," *J. Exp. Med.*, The Rockefeller University Press, 1990, vol. 171, 1375–1380.

G.J. Adema, A.J. de Boer, A.M. Vogel, W.A.M. Loenen, and C.G. Figdor, "Molecular Characterization of the Melanocyte Lineage–specific Antigen gp100," *The Journal of Biological Chemistry*, The American Society for Biochemistry and Molecular Biology, Inc., 1994, vol. 269, No. 31, Issue of Aug. 5, pp. 20126–20133.

S.h. Park, Y.M. Bae, H.J. Kwon, T.J. Kim, J. Kim, S.J. Lee, and S.K. Lee, "JL1, A Novel Differentiation Antigen of Human Cortical Thymocyte," *J. Exp. Med.*, Rockefeller University Press, 1993, vol. 178, pp. 1447–1451.

S. Krishnan, J. Haensler, and P. Meulien, "Paving the Way Towards DNA Vaccines," *Nature Medicine*, 1995, vol. 1, No. 6, pp. 521–522.

B. Bouchard, S. Vijayasaradhi, and A.N. Houghton, "Production and Characterization of Antibodies Against Human Tyrosinane," The Journal of Investigative Dermatology, 1994, vol. 102, No. 3, pp. 291–295.

S.L. Barclay and A.M. Smith, "Rapid Isolation of Monoclonal Antibodies Specific for Cell Surface Differentiation Antigens" *Proc. Natl. Acad. Sci, USA*, 1986, vol 83, pp. 4336–4340.

* cited by examiner

METHOD AND COMPOSITIONS FOR STIMULATION OF AN IMMUNE RESPONSE TO A DIFFERENTIATION ANTIGEN STIMULATED BY AN ALTERED DIFFERENTIATION ANTIGEN

This application is a 371 of International Application No. PCT/US97/22669, filed Dec. 10, 1997, and claims the benefit of U.S. Provisional Applications Nos. 60/032,535 filed Dec. 10, 1996 and 60/036,419 filed Feb. 18, 1997.

BACKGROUND OF THE INVENTION

This application relates to a method and compositions for stimulation of an immune response to differentiation antigens.

Differentiation antigens are tissue-specific antigens that are shared by autologous and some allogeneic tumors of similar derivation, and on normal tissue counterparts at the same stage of differentiation. Differentiation antigens have been shown to be expressed by a variety of tumor types, including melanoma, leukemia, lymphomas, colorectal, carcinoma, breast carcinoma, prostate carcinoma, ovarian carcinoma, pancreas carcinomas, and lung cancers. For example, differentiation antigens expressed by melanoma cells include Melan-A/MART-1, Pmel 17, tyrosinase, and gp75. Differentiation antigen expressed by lymphomas and leukemia include CD19 and CD20/CD20 B lymphocyte differentiation markers). An example of a differentiation antigen expressed by colorectal carcinoma, breast carcinoma, pancreas carcinoma, prostate carcinoma, ovarian carcinoma, and lung carcinoma is the mucin polypeptide muc-1. A differentiation antigen expressed by breast carcinoma is her2/neu. The her2/neu differentiation antigen is also expressed by ovarian carcinoma. Differentiation antigens expressed by prostate carcinoma include prostate specific antigen, prostatic acid phosphatase, and prostate specific membrane antigen.

Melanocyte differentiation antigens have been shown to be recognized by autoantibodies and T cells of persons with melanoma, and to be relevant autoantigens. Wang et al., *J. Exp. Med.* 183: 799–804 (1996); Vijayasaradhi et al.,*J. Exp. Med.* 171: 1375–1380 (1990). Unfortunately, in most cases, the immune system of the individual is tolerant of these antigens, and fails to mount an effective immune response. For the treatment of cancers where the tumor expresses differentiation antigens therefore, it would be desirable to have a method for stimulating an immune response against the differentiation antigen in vivo. It an object of the present invention to provide such a method.

SUMMARY OF THE INVENTION

It has now been found that the tolerance of the immune system for self differentiation antigens can be overcome and an immune response stimulated by administration of a therapeutic differentiation antigen. The therapeutic differentiation antigen is altered with respect to the target differentiation antigen in the individual being treated (i.e., the differentiation antigen to which an immune response is desired) in one of three ways. First, the therapeutic differentiation antigen may be syngeneic with the target differentiation antigen, provided that therapeutic differentiation antigen is expressed in cells of a species different from the individual being treated. For example, a human differentiation antigen expressed in insect or other non-human host cells can be used to stimulate an immune response to the differentiation antigen in a human subject. Second, the therapeutic differentiation antigen may be a mutant form of a syngeneic differentiation antigen, for example a glycosylation mutant. Third, the therapeutic differentiation antigen may be a differentiation antigen (wild-type or mutant) of the same type from a species different from the individual being treated. For example, a mouse differentiation antigen can be used to stimulate an immune response to the corresponding differentiation antigen in a human subject. Administration of altered antigens in accordance with the invention results in an effective immunity against the original antigen expressed by the cancer in the treated individual.

A further aspect of the invention are certain compositions and cell lines which are useful in practicing the method of the invention. In particular, the invention includes non-human cell lines, for example insect cell lines, expressing a human differentiation antigen and expression vectors useful in generating such cell lines.

DETAILED DESCRIPTION OF THE INVENTION

Figure 1:
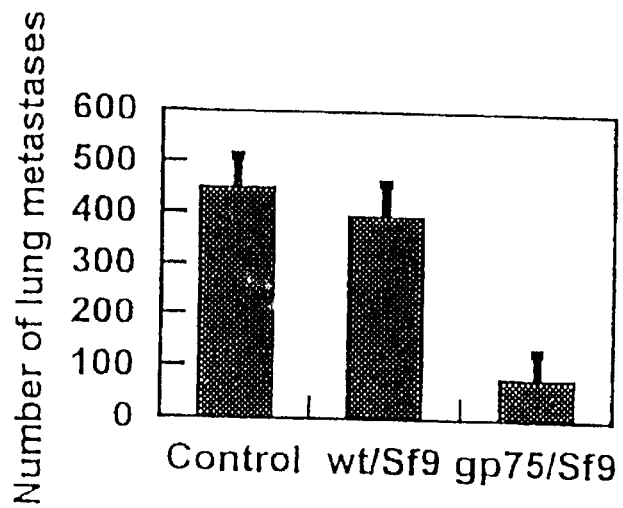
FIG. 1 summarizes the results of a tumor protection experiment using mice immunized with human gp75 expressed in Sf9 insect cells.

The present invention provides a method for stimulating an immune response to a tissue expressing a target differentiation antigen in a subject individual. The subject individual is preferably human, although the invention can be applied in veterinary applications to animal species, preferably mammalian or avian species, as well.

As used in the specification and claims of this application, the term "immune response" encompasses both cellular and humoral immune responses. Preferably, the immune response is sufficient to provide immunoprotection against growth of tumors expressing the target differentiation antigen. The term "stimulate" refers to the initial stimulation of a new immune response or to the enhancement of a pre-existing immune response.

In accordance with the invention, a subject individual is treated by administering a therapeutic differentiation antigen of the same type as the target differentiation antigen in an amount effective to stimulate an immune response. Thus, for example, if the target differentiation antigen is the gp75 antigen found in melanoma cells and melanocytes, the therapeutic antigen is also a gp75 antigen. It has been found experimentally, however, that administration of syngeneic differentiation antigens expressed in cells of the same species as the subject individual are not effective for stimulating an immune response (See Examples 1 and 2). Thus, to be effective in the method of the invention, the therapeutic differentiation antigen must be altered relative to the target differentiation.

In a first embodiment of the invention, the therapeutic differentiation antigen and the target are both from the same species. The therapeutic differentiation antigen is produced by expression in cells of a second species different from the first species. In a second embodiment of the invention, the therapeutic differentiation antigen is a mutant form of a syngeneic differentiation antigen. In a third embodiment of the invention, the therapeutic differentiation antigen is a xenogeneic differentiation antigen. Each of these embodiments will be discussed in turn below.

Administration of the therapeutic differentiation antigen can be accomplished by several routes. First, the therapeutic differentiation antigen may be administered as part of a vaccine composition which may include one or more adjuvants such as alum, QS21, TITERMAX or its derivatives, incomplete or complete Freund's and related adjuvants, and cytokines such as granulocyte-macrophage colony stimulating factor, flt-3 ligand, interleukin-2, interleukin4 and interleukin- 12 for increasing the intensity of the immune response. The vaccine composition may be in the form of a therapeutic differentiation antigen in a solution or a suspension, or the therapeutic differentiation antigen may be introduced in a lipid carrier such as a liposome. Such compositions will generally be administered by subcutaneous, intradermal or intramuscular route. Vaccine compositions containing expressed therapeutic differentiation antigen are administered in amounts which are effective to stimulate an immune response to the target differentiation antigen in the subject individual. The preferred amount to be administered will depend on the species of the target individual and on the specific antigen, but can be determined through routine preliminary tests in which increasing doses are given and the extent of antibody formation or T cell response is measured by ELISA or similar tests. T cell responses may also be measured by cellular immune assays, such as cytotoxicity, cytokine release assays and proliferation assays.

The mutant syngeneic or xenogeneic therapeutic differentiation antigen may also be introduced in accordance with the invention using a DNA immunization technique in which DNA encoding the antigen is introduced into the subject such that the antigen is expressed by the subject.

Syngeneic Antigen Expressed in Cells of Different Species

In accordance with the present invention, an immune response against a target differentiation antigen can be stimulated by the administration of syngeneic differentiation antigen expressed in cells of a different species. In general, the subject being treated will be a human or other mammal. Thus, insect cells are a preferred type of cells for expression of the syngeneic differentiation antigen. Suitable insect cells lines includes Sf9 cells and Schneider 2 Drosophila cells. The therapeutic differentiation antigen could also be expressed in bacteria, yeast or mammalian cell lines such as COS or chinese hamster ovary cells. Host cells which are evolutionarily remote from the subject being treated, e.g. insects, yeast or bacteria for a mammalian subject, may be preferred since they are less likely to process the expressed protein in a manner identical to the subject.

To provide for expression of the differentiation antigen in the chosen system, DNA encoding the differentiation antigen or a portion thereof sufficient to provide an immunologically effective expression product is inserted into a suitable expression vector. There are many vector systems known which provide for expression of incorporated genetic material in a host cell, including baculovirus vectors for use with insect cells, bacterial and yeast expression vectors, and plasmid vectors (such as psvk3) for use with mammalian cells. The use of these systems is well known in the art.

For treatment of humans with a syngeneic differentiation antigen, cDNA encoding the human differentiation antigen to be targeted must be available. cDNA is produced by reverse transcription of mRNA, and the specific cDNA encoding the target differentiation antigen can be identified from a human cDNA library using probes derived from the protein sequence of the differentiation antigen. The cDNA sequences of various human differentiation antigens have been derived by these methods and are known in the art. For example, the sequence of human gp75 (also known as Tyrosinase-related Protein-1) is known from Vijayasaradhi, S., Bouchard, B., Houghton, A. N., "The Melanoma Antigen Gp75 Is the Human Homologue of the Mouse B (Brown) Locus Gene Product",. *J. Exp. Med.* 171: 1375–1380 (1990); Bouchard et al., *J. Exp. Med.* 169: 2029–2042 (1989). Other human differentiation antigens with known cDNA sequences are gp 100 (also known as tyrosinase-related protein-2) (Kawakami et al, *Proc. Nat'l. Acad. Sci.* (*USA*) 91: 6458–6462 (1994); Adema et al., *J. Biol. Chem.* 269: 20126–20133 (1994), and mart-1/melan-a for malignant melanoma; CD19 and CD20 for non-Hodgkin's lymphoma; her-2/neu for breast carcinoma (King et al., *Science* 229: 874–976 (1985); muc-1 for breast, colorectal, lung and pancreatic carcinomas (Spicer et al., *J. Biol. Chem.* 266: 15099–15109 (1991)); prostate specific membrane antigen, prostate specific antigen, and prostatic acid phosphatase for prostate carcinoma (Israeli et al., *Cancer Res.* 54: 6344–6347 (1994); Monne et al., *Cancer Res.* 54: 6344–6437 (1994); Vihko et al., *FEBS Lett.* 236: 275–281 (1988)).

The therapeutic differentiation antigen expressed in cells of a different species is administered to the subject individual in an amount effective to induce an immune response. The composition administered may be a lysate of cells expressing the therapeutic differentiation antigen, or it may be a purified or partially purified preparation of the therapeutic differentiation antigen.

Mutant forms of Syngeneic Differentiation Antigen

In the second embodiment of the invention, a mutant form of a syngeneic differentiation antigen of a type expressed by the target tumor is used to stimulate an immune response directed against the tumor. For example, if the tumor is a human tumor that expresses gp75, then a mutant form of human gp75 is used as the therapeutic differentiation antigen.

It will be appreciated by persons skilled in the art that not all mutations will produce an antigen which is useful in the method of the present invention. For example, large-scale deletions which eliminate important epitopes would not be expected to work and are not considered to be therapeutic differentiation antigens as that term is used in the specification and claims of this application. Less extensive mutations, however, particularly those which alter the tertiary and/or quaternary structure of the expressed differentiation antigen are within the scope of the present invention.

A preferred type of mutant form of therapeutic differentiation antigen is a glycosylation mutant. On any given membrane protein, there will generally be one or multiple glycosylation sites, with each site being of different importance in its effect on the transport and degradation of the protein. For example, in the case of mouse gp75, there are six N-glycosylation sites, one of which strongly effects the resistance to protease digestion and two others of which are important for permitting export of the protein from the endoplasmic reticulum. Glycosylation-mutants that are altered at these sites (Asn 96, Asn 104, Asn 181, Asn 304, Asn 350, Asn 385) have been prepared using site-directed mutagenesis. These mutations result in the conversion of syngeneic proteins which are normally non-immunogenic into immunogenic altered antigens.

Genetic immunization with a glycosylation mutant syngeneic gp75 where asparagine at amino acid position 350 is altered to delete the glycosylation site at this position was found to stimulate production of autoantibodies against an intracellular, early processed form of gp75. These autoantibodies did not recognize mature gp75. We have generated these same antibodies by immunizing with cells expressing this altered protein, i.e., immunization with the altered protein has the same effect.

Xenogeneic Differentiation Antigens

In accordance with the present invention, an immune response against a target differentiation antigen can be stimulated by the administration of xenogeneic differentiation antigen of the same type. Thus, for example, an immune response to tumor that expresses gp75 can be stimulated by immunization with gp75 derived from a different species which breaks the tolerance to the autoantigen. For treatments of humans, preferred xenogeneic antigens will be rodent antigens, but could come from other mammals such as dog, cat, cow, or sheep, or from birds, fish, amphibian, reptile, insect or other more distantly related species.

Xenogeneic differentiation antigen may be administered as a purified differentiation antigen derived form the source organism. Proteins can be purified for this purpose from cell lysates using column chromatography procedures. Proteins for this purpose may also be purified from recombinant sources, such as bacterial or yeast clones or mammalian or insect cell lines expressing the desired product. Nucleic acid sequences of various differentiation antigens from various non-human sources are known, including mouse tyrosinase (gp75) (Yamamoto et al., *Japanese J. Genetics* 64: 121–135 (1989)); mouse gp100 (Bailin et al., *J. Invest. Dermatol.* 106: 24–27 (1996)); and rat prostate-specific membrane antigen (Bzdega et al., *J. Neurochem.* 69: 2270–2277 (1997).

Xenogeneic differentiation antigen may also be administered indirectly through genetic immunization of the subject with DNA encoding the differentiation antigen. cDNA encoding the differentiation antigen is combined with a promoter which is effective for expression of the nucleic acid polymer in mammalian cells. This can be accomplished by digesting the nucleic acid polymer with a restriction endonuclease and cloning into a plasmid containing a promoter such as the SV40 promoter, the cytomegalovirus (CMV) promoter or the Rous sarcoma virus (RSV) promoter. The resulting construct is then used as a vaccine for genetic immunization. The nucleic acid polymer could also be cloned into plasmid and viral vectors that are known to transduce mammalian cells. These vectors include retroviral vectors, adenovirus vectors, vaccinia virus vectors, pox virus vectors and adenovirus-associated vectors.

The nucleic acid constructs containing the promoter, antigen-coding region and intracellular sorting region can be administered directly or they can be packaged in liposomes or coated onto colloidal gold particles prior to administration. Techniques for packaging DNA vaccines into liposomes are known in the art, for example from Murray, ed. "Gene Transfer and Expression Protocols" Humana Pres, Clifton, N.J. (1991). Similarly, techniques for coating naked DNA onto gold particles are taught in Yang, "Gene transfer into mammalian somatic cells in vivo", *Crit. Rev. Biotech.* 12: 335–356 (1992), and techniques for expression of proteins using viral vectors are found in Adolph, K. ed. "Viral Genome Methods" CRC Press, Florida (1996).

For genetic immunization, the vaccine compositions are preferably administered intradermally, subcutaneously or intramuscularly by injection or by gas driven particle bombardment, and are delivered in an amount effective to stimulate an immune response in the host organism. The compositions may also be administered ex vivo to blood or bone marrow-derived cells (which include APCs) using liposomal transfection, particle bombardment or viral infection (including co-cultivation techniques). The treated cells are then reintroduced back into the subject to be immunized. While it will be understood that the amount of material needed will depend on the immunogenicity of each individual construct and cannot be predicted a priori, the process of determining the appropriate dosage for any given construct is straightforward. Specifically, a series of dosages of increasing size, starting at about 0.1 ug is administered and the resulting immune response is observed, for example by measuring antibody titer using an ELISA assay, detecting CTL response using a chromium release assay or detecting TH (helper T cell) response using a cytokine release assay.

The invention will now be further described with reference to the following, non-limiting examples.

EXAMPLE 1

C57BL/6 mice were immunized with a) syngeneic gp75$^+$ B16 melanoma cells (which express a non-mutant b locus protein); b) syngeneic B16 cells expressing IL-2, GM-CSF and IFN-γ; c) syngeneic gp75$^-$ B16 melanoma variant, B78H.1 and syngeneic fibroblasts transfected with cDNA expressing the mouse b allele; d) hydrophilic peptides of gp75 conjugated to carrier protein; and e) full length gp75 glycoprotein purified from syngeneic melanoma cells. Cells, purified glycoprotein or peptides were combined with adjuvants, including Freund's adjuvant, a mixture of bacterial cell wall skeletons and an endotoxin derivative (DETOX), and a saponin component (QS21). Immunizations were tested by intraperitoneal, subcutaneous and intradermal routes. After immunizations, mice were assessed for antibodies against gp75 by ELISA, inmmunoprecipitation and Western blots, and for cytotoxic T lymphocytes (CTL) to B16 using a $^{51}$Cr-release cell-mediated cytotoxicity assay. As summiarized in Table 1, no antibodies or CTL against gp75 were detected after any of these immunization strategies, supporting the conclusion that C57BL/6 maintain tolerance to the gp75 glycoprotein.

EXAMPLE 2

As shown in Example 1, syngeneic C57BL/6 mice immunized with either cell-associated or purified forms of gp75 protein did not produce autoantibodies to gp75. We next assessed whether gp75 encoded by cDNA delivered into the dermis of syngeneic C57BL/6 mice by particle bombardment would induce an autoantibody response.

C57BL/6 mice were genetically immunized with cDNA encoding full-length syngeneic gp75 under the control of a CMV promoter once a week for five weeks. Sera from these mice were then assessed for autoantibodies against gp75 by immunoprecipitation as described in the Materials and Methods. No mouse (0/28) had detectable antibodies, indicating that C57BL/6 mice maintained their tolerance to the syngeneic protein.

EXAMPLE 3

A baculovirus expression vector encoding full length murine gp75 was constructed and isolated in collaboration with Dr. Charles Tackney (Imclone, New York, N.Y.) using standard techniques. Summers & Smith, "A manual for methods for baculovirus vectors and insect cell culture procedures", *Texas Agricultural Experiment Station Bulletin*

No 1555 (1987); Luckow & Summers, *Biotechnology* 6:47–55 (1988). Briefly, the 1.8 kb EcoRI fragment of pHOMERB2 encoding murine gp75 was subcloned into a baculovirus expression vector related to pBbac produced by Stratagene, Inc, and the expression vector introduced into baculovirus. *Spodoptera frugiperda* Sf9 insect cells were coinfected with this virus construct and wild-type *Autographa californica* nuclear polyhedrosis virus (AcNPV) and recombinant AcNPV expressing mouse gp75 was generated by homologous recombination. After plaque purification, Sf9 cells were infected with the recombinant virus and clones expressing high levels of gp75 were identified by screening with an antibody against gp75. These cell lines were used for immunization studies.

C57BL/6 mice were immunized with lysates of insect Sf9 cells expressing either syngeneic gp75 in a baculovirus vector (gp75/Sf9) or wild-type baculovirus (wt/Sf9). Mice immunized with gp75/Sf9 lysates (1 or $5\times10^6$ cells) developed autoantibodies to gp75 with (120/120 mice) or without (25/28 mice) Freund's adjuvant. No antibodies were detected after immunization with wt/Sf9 (0 of 46 mice). Autoantibodies appeared after two to four immunizations, lasted for more than four months after the last immunization, and reacted with gp75 expressed in syngeneic melanocytic cells (B16F10 and JBRH melanomas). Antibodies were IgG class, based on reactivity with rabbit anti-mouse IgG and protein A, and copurification of antibody reactivity with IgG fractions from sera.

The difference in immunogenicity between gp75/Sf9 and mouse gp75 was not due simply to quantitative differences in the amount of gp75 in the two preparations. $8\times10^6$ B16 melanoma cells contained 20 µg of gp75, compared to only 14 µg in $1\times10^6$ gp75/Sf9 cells. Also, 10 µg of purified mouse gp75 mixed with wt/Sf9 lysates did not induce autoantibodies. Although Sf9 cells can apparently provide an adjuvant effect (Prehaud et al., *Virology* 173: 390–399 (1989); Ghiasi et al., *J. Gen. Virology* 73: 719–722 (1992)), these results show that other differences between gp75 produced in mouse cells versus insect cells (for instance carbohydrate structures) were necessary to induce autoantibodies.

EXAMPLE 4

In contrast to immunization with gp75/Sf9 lysates, immunization with purified gp75 (12 µg) produced in gp75.Sf9 insect cells plus Freund's adjuvant induced autoantibodies that recognized 68/70 kDa early processed forms of gp75. This form of gp75 contained only immature, high mannose N-linked carbohydrates, which results in localization of the molecule to the endoplasmic reticulum or cis Golgi compartment.

EXAMPLE 5

Mice were immunized with the gp75$^+$ human melanoma cell line SK-MEL-19 with Freund's adjuvant and evaluated for the development of autoantibodies to murine gp75. All of the mice (20/20) developed autoantibodies. There was no response without adjuvant (0/5 mice), and no antibodies to gp75 were detected in sera of 12 mice immunized with gp75$^-$ human melanomas SK-MEL-131 or SK-MEL-37 plus Freund's adjuvant. Three of five mice immunized with purified human gp75 (10 µg per dose for five immunizations) with Freund's adjuvant developed autoantibodies to gp75, although the antibody responses were generally weaker, possibly due to the lower amount of purified gp75 used compared to the amount of gp75 in SK-MEL-19 lysates. Thus, administration of human gp75 broke the tolerance to gp75 in C57BL/6 mice.

EXAMPLE 6

B16 melanoma cells and normal melanocytes in C57BL/6 mice express GP75, the wild-type b allele of the brown locus. As described above, the product of this locus is recognized by sera from syngeneic mice immunized with mouse gp75 expressed in gp75/Sf9 cells and human gp75. We have previously shown that passive transfer of mouse monoclonal antibody against gp75 into mice bearing B16F10 tumors leads to tumor rejection. Hara et al., *Int. J. Cancer* 61: 253–260 (1995). To determine whether the autoimmune responses observed conferred similar protection against tumors, the in vivo effects of immune recognition of gp75 were investigated using a syngeneic tumor model.

Mice (5 mice per group) were injected subcutaneously with gp75/Sf9 lysates ($5\times10^6$ gp75/Sf9 cells) concurrently with $10^5$ B16F10 melanoma cells administered intravenously and the occurrence of lung metastases 14 days after tumor challenge was monitored. Mice immunized with wt/Sf9 cells and unimmunized mice were used as controls. The results are summarized in FIG. 1. As shown, mice immunized with gp75/Sf9 lysates were substantially protected against formation of lung metastases compared to the controls. Significant protection (53% decrease in lung metastases) was also observed when immunization was carried out 4 days after the tumor challenge as metastases become established. There was no significant protection in mice immunized with wt/Sf9 lysates compared to the unimmunized control.

Passive transfer of serum from mice immunized with gp75/Sf9 to five unimmunized mice produced a 68% decrease in lung metastases compared to mice treated with an equivalent amount of normal mouse serum (p=0.02), supporting the conclusion that tumor protection was at least partially mediated by humoral mechanisms.

Mice immunized with human gp75$^+$ SK-MEL-19 were also markedly protected against B16F10 melanoma compared to unimmunized mice. (4+/−7 metastases in immunized mice versus 275+/−77 lung metastases in control mice—6 mice per group). Immunization with gp75$^-$ melanoma SK-MEL-131 did not introduce tumor protection against B16F10 melanoma, although recognition of other xenogeneic antigens other than gp75 could not be critically assessed.

Mice immunized against the immature, early processed form of gp75, using purified gp75 from gp75/Sf9 cells were not significantly protected against B16F10 metastases (366+/−78 metastases in four immunized mice versus 412+/−94 metastases in five unimmunized control mice). However one mouse in this group did eventually develop autoantibodies against mature gp75 and was protected against lung metastases (only 21 metastases).

EXAMPLE 7

C57BL/6 mice were genetically immunized with cDNA encoding full length human gp75 under control of the control of a CMV promoter once a week for five weeks by gene gun injection. As controls, mice were injected with full length syngeneic mouse gp75 under the control of the CMV promoter, with a glycosylation mutant of gp75 (gly31) or null DNA. Four weeks after the final immunization, the mice were injected through the tail vein with $2\times10^5$ B16F10LM3 melanoma cells. One group of treated mice were also challenged with melanoma cells. Twenty-one days after tumor challenge, mice were sacrificed and surface metastatic lung nodules were scored. There were ten mice in the untreated group, 9 mice in each of the null and mouse gp75 groups, 8 mice in the gly31 group and 19 mice in the human gp75 group. The importance of CD4, CD8 and NK cells was also tested by depletion of using monoclonal antibodies (rat mAb GK1.5 for CD4; mAb 53.6.7 for CD8 and mAb PK1.36 for NK1.1). The necessity of CD4 T cells was also assessed by looking for tumor rejection in CD4 knock-out mice after in vivo transfer of the human gp75 gene by gene gun.

Figure 2:
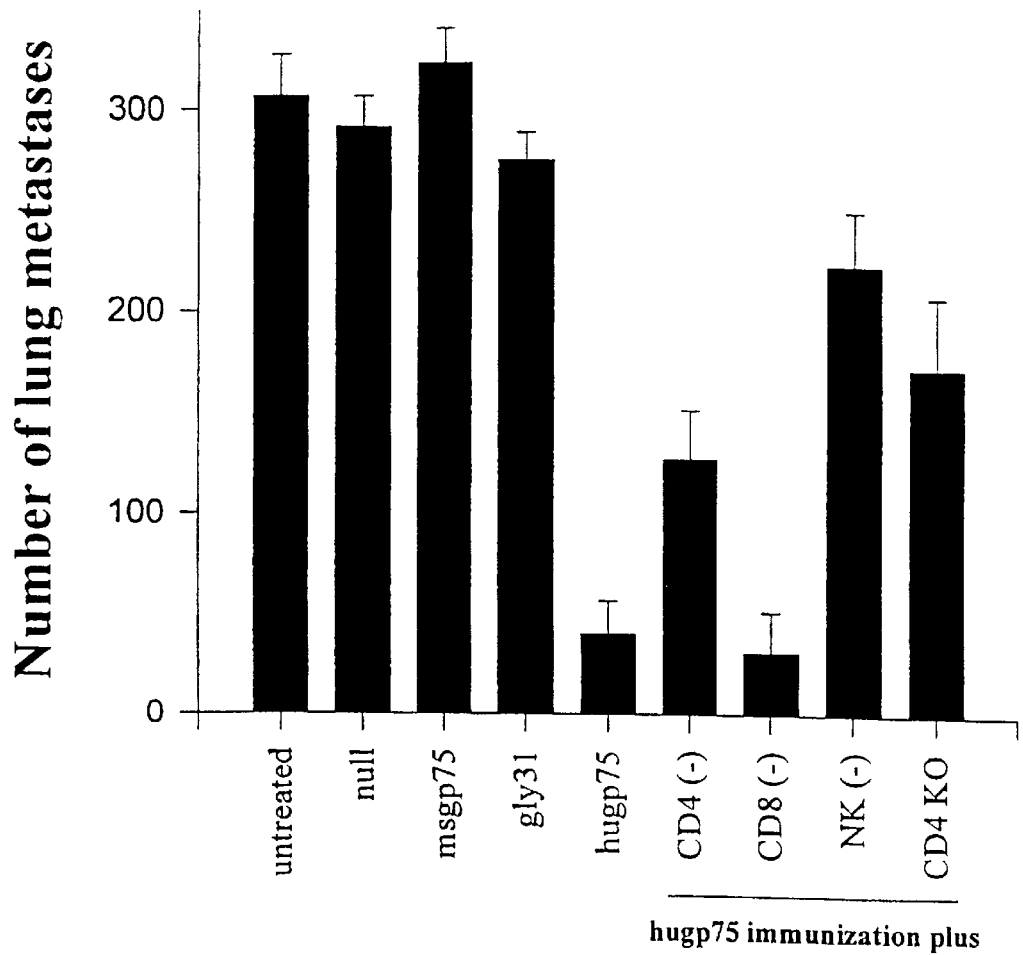
FIG. 2 summarizes the results of a tumor protection using mice immunized by gene gun with DNA encoding xenogeneic human gp75.

As shown in FIG. 2, mice immunized with xenogeneic human gp75 were found to be significantly protected from lung metastases (mean 41±15 metastases) when challenged with B16F10LM3 melanoma (p<0.0001), with an 84% decrease in lung nodules as compared with control mice. Syngeneic mice that received in vivo gene transfer of the glycosylation mutant mouse gp75 were not significantly protected from B16F10LM3 tumor challenge (mean 300±12 metastases), nor were those that were delivered control DNA (mean 292±15 metastases) by particle bombardment or were left untreated (mean 307±20 metastases) (p>0.45). CD8 deletion did not alter tumor rejection, although depletion of $CD4^+$ (by mAb or knock-out) and $NK1.1^+$ cells did result in a reduction in level of protection achieved. Thus these latter cells may play a role in the protection against tumors achieved using genetic immunization with xenogeneic DNA.

What is claimed is:

1. A method for stimulating an immune response to a tissue expressing a target differentiation antigen in a subject individual of a first species, comprising administering to the subject individual an immunologically-effective amount of a therapeutic differentiation antigen of the same type as the target differentiation antigen, wherein the therapeutic differentiation antigen is produced by expression in cells of a second species different from the first species.

2. The method according to claim 1, wherein the subject individual of the first species is human.

3. The method according to claim 2, wherein the therapeutic differentiation antigen is a human differentiation antigen.

4. The method according to claim 3, wherein the therapeutic differentiation antigen is expressed in insect cells.

5. The method according to claim 2, wherein the therapeutic differentiation antigen is a non-human differentiation antigen.

6. The method according to claim 5, wherein the therapeutic differentiation antigen is a mouse differentiation antigen.

7. The method according to claim 2, wherein the target differentiation antigen is expressed in melanocytes of the subject individual.

8. The method according to claim 7, wherein the therapeutic differentiation antigen is a human differentiation antigen.

9. The method according to claim 8, wherein the therapeutic differentiation antigen is expressed in insect cells.

10. The method according to claim 7, wherein the therapeutic differentiation antigen is a non-human differentiation antigen.

11. The method according to claim 10, wherein the therapeutic differentiation antigen is a mouse differentiation antigen.

12. A method for stimulating an immune response to a tissue expressing a target differentiation antigen in a subject individual of a first species, comprising administering to the subject individual an immunologically-effective amount of a therapeutic differentiation antigen of the same type derived from a second species different from the first species.

13. A non-human cell line expressing a human differentiation antigen.

14. The cell line of claim 13, wherein the cell line is an insect cell line.

15. The cell line of claim 13, wherein the human differentiation antigen is derived from human melanocytes.

16. The cell line of claim 15, wherein the cell line is an insect cell line.

17. The cell line of claim 15, wherein the human differentiation antigen is gp75.

18. An expression vector comprising a DNA sequence encoding a human differentiation antigen and a promoter region effective to promote expression of the human differentiation antigen in insect cells.

19. The vector of claim 18, wherein the expression vector comprises a baculovirus promoter region.

* * * * *